United States Patent [19]

Rubens

[11] Patent Number: 4,463,762

[45] Date of Patent: Aug. 7, 1984

[54] APPARATUS FOR OBTAINING AN OBJECTIVE DETERMINATION OF THE RATE OF OXYGEN UTILIZATION IN PERIPHERAL TISSUE

[75] Inventor: Harry E. Rubens, Bay Harbor Islands, Fla.

[73] Assignee: Institute of Applied Biology Special Cancer Research Project, Bay Harbor Islands, Fla.

[21] Appl. No.: 132,994

[22] Filed: Mar. 24, 1980

Related U.S. Application Data

[63] Continuation-in-part of Ser. No. 843,270, Oct. 18, 1977, Pat. No. 4,222,389.

[51] Int. Cl.³ ............................................. A61B 5/00
[52] U.S. Cl. ................................... 128/633; 128/666; 356/41
[58] Field of Search ............................. 128/633, 666; 356/39-41, 308

[56] References Cited

U.S. PATENT DOCUMENTS

| | | | |
|---|---|---|---|
| 2,824,972 | 2/1958 | Beitz | 356/308 |
| 3,152,587 | 10/1964 | Ullrich et al. | 128/633 |
| 3,486,822 | 12/1969 | Harris | 356/308 |
| 3,810,460 | 5/1974 | Van Nie | 128/666 |
| 4,000,972 | 1/1977 | Braun et al. | 356/39 |
| 4,086,915 | 5/1978 | Kofsky et al. | 128/633 |
| 4,281,645 | 8/1981 | Jöbsis | 128/633 |

OTHER PUBLICATIONS

Janssen, F. J., *Medicamundi*, vol. 17, No. 1, (1972), pp. 7-15.

Laing, R. A. et al., *IEEE Trans. on Biomed. Engng.*, vol. BME-22, No. 3, May 1975.

Primary Examiner—Kyle L. Howell
Assistant Examiner—Francis J. Jaworski
Attorney, Agent, or Firm—Just, Rubens & Howe

[57] ABSTRACT

Apparatus employing a non-invasive method for objectively determining in vivo, the rate of oxygen utilization in peripheral tissue by spectral measuring means, containing a light source, a clamp or tourniquet for occluding a segment of blood in the tissue, means for transmitting the light through the isolated segment of blood to pick up the spectral values of the oxyhemoglobin for two selected wavelengths, wherein the rate of reduction of the oxyhemoglobin of the blood as determined at one wavelength is faster that the rate of reduction of the oxyhemoglobin at the other wavelength, means for converting the spectral values individually for the two selected wavelengths into current flow, and means for determining the time-space relationship between the changing spectral values of the two selected wavelengths, from the moment of occlusion.

10 Claims, 4 Drawing Figures

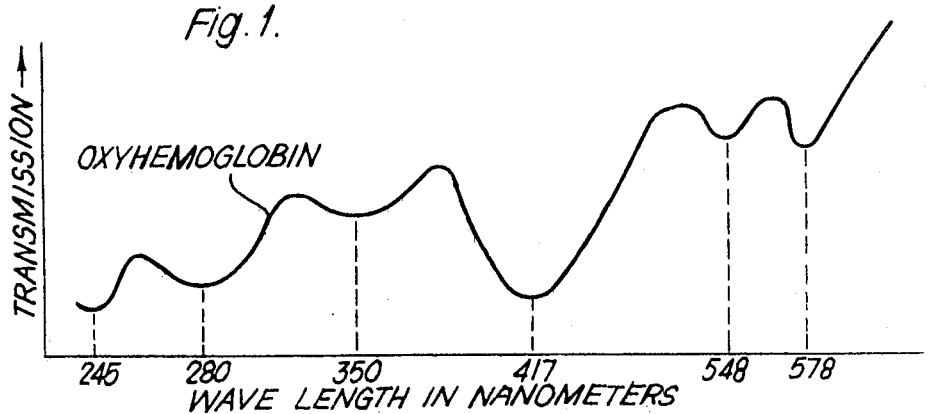
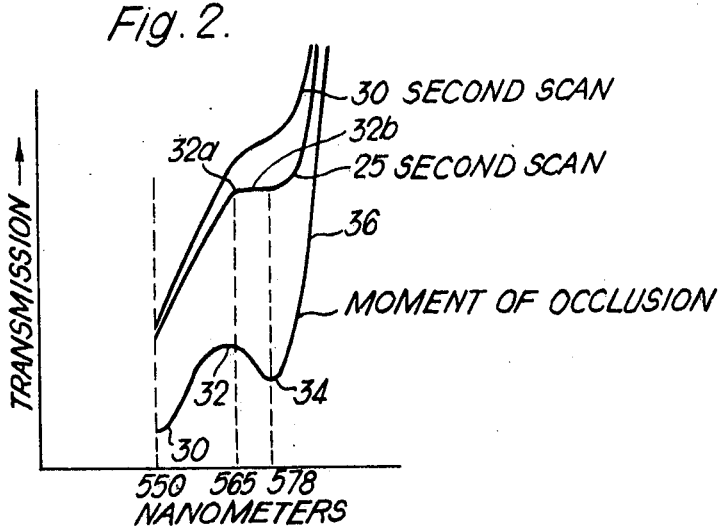
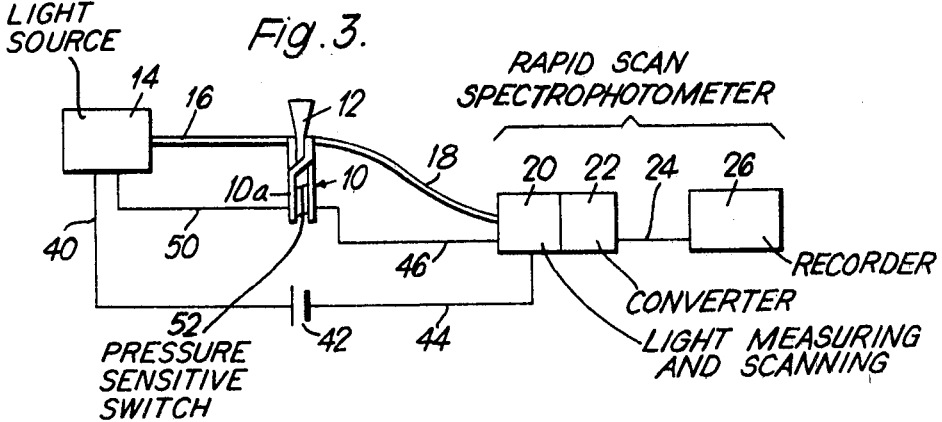

APPARATUS FOR OBTAINING AN OBJECTIVE DETERMINATION OF THE RATE OF OXYGEN UTILIZATION IN PERIPHERAL TISSUE

This invention relates to apparatus for determining the rate of oxygen utilization in tissue, and more particularly to its determination by spectral means, and this application is a continuation in part of parent application Ser. No. 843,270, filed Oct. 18, 1977, now U.S. Pat. No. 4,222,389 dated Sept. 16, 1980.

The spectral phenomena of oxyhemoglobin has been known since 1875 when it was reported by K. Vierordt in Physiologische Spectralanalysen Zeitrschrift fur Biologie, 1875, pp 187–197; 1878, pp, 422–448. However no extensive use has been made to utilize the phenomena which requires great subjective skill and visual acuity possessed by few persons. Thus the phenomena is practically unknown in the medical field except for its application in oximetry for determining the approximate oxygen content of the blood during operative procedures.

The rate of oxygen utilization represents the summation of many chemical activities in the body; examples being the hormonal system and the enzymes used in the oxidation-reduction process. With an accurate and sensitive measurement of oxygen utilization, it is possible to determine that one or more of the multiple factors which contribute to body metabolism, are out of balance, and to evaluate the remedial procedures that should be initiated to locate and correct the imbalance.

Thus, if the change in the rate of oxygen utilization is in the direction of homeostasis, the diagnosis and procedure would appear to be relevant. If however, the rate is exacerbated or unchanged, the remedial procedures should be deemed to be valueless in correcting the imbalance.

Accordingly, the principal object of the present application, is to provide an apparatus for measuring objectively, the rate of oxygen utilization in tissue, non-invasively, using spectrometric means. Other objects are to determine those regions on the spectral curve for oxyhemoglobin, which under occlusion, show a rate of change greater than other adjacent regions on the same curve; to provide a scan of the spectral curve for oxyhemoglobin, continuously repeated through selected regions, at selected time intervals, so that the time-space changes in the reproduced curves, indicates the relative changes in the oxygen content of the hemoglobin, for the specified period of time; to select those regions on the spectral curve for oxyhemoglobin which appears to be the most sensitive to inner change for use as a standard for determining the rate of oxygen utilization; to provide such an apparatus which employs two selected regions of wavelengths which show the greatest time-space changes; and to provide the apparatus with electronic means for comparing the changing spectral values of the selected regions of wavelengths, and for stopping an electric timer when the spectral values of the two regions of wavelengths are equal.

These and other objects are achieved, and new results obtained, as will be evident from a consideration of the following description, claims, and drawings, in which:

FIG. 1 is a spectral curve for oxyhemoglobin showing the relative light transmission for all wavelengths from about 240 to about 600 nanometers.

FIG. 2 shows successive spectral curves of oxyhemoglobin from the moment of tissue occlusion to the 30 second scan, in the 550–600 nanometer region.

FIG. 3 is a schematic diagram of a light transmitting and measuring apparatus that may be used to provide the rapid scan spectral curves for oxyhemoglobin illustrated in FIG. 2.

Figure 4:
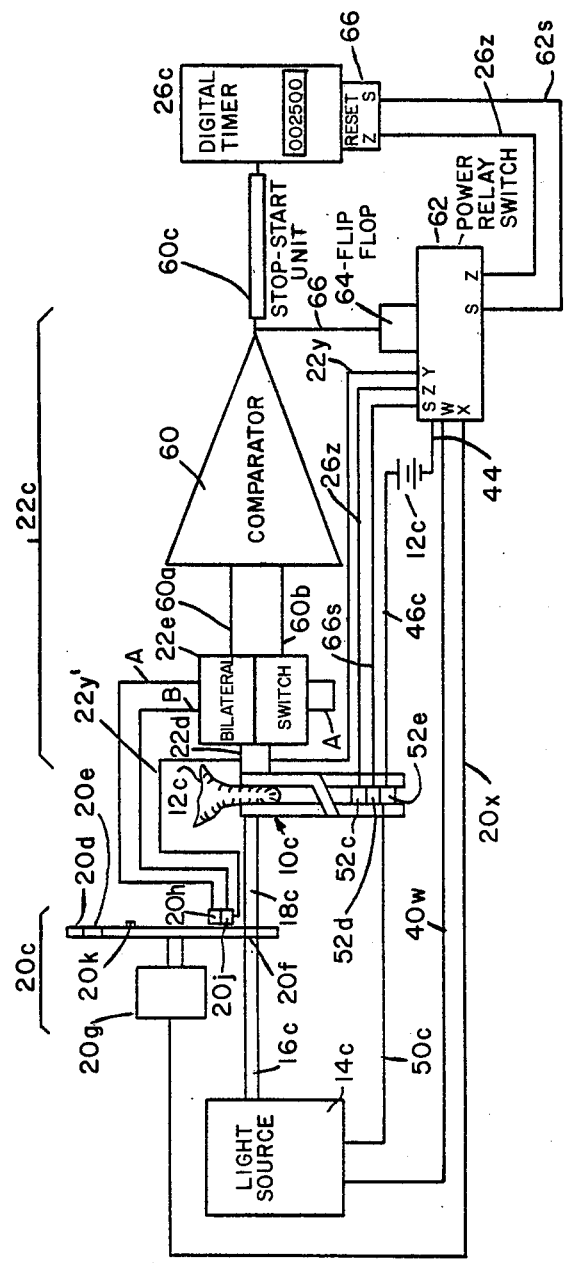
FIG. 4 is a schematic diagram showing another light transmitting and measuring apparatus, which employs two filters for selecting the two regions whose spectral signals are compared for stopping an electronic timer when the signals are equalized.

I employ for my purpose, an interdigital clamp 10, shown in FIG. 3. which is similar in nature to a hemostat, containing an aperture in the clamping jaws, to allow light to pass therethrough. The locking pressure of the clamp will isolate a segment of blood within the apertured area which may be about 5 mm in diameter, when the clamp is applied to the interdigital fold of skin on the hand. The pressure is sufficient to keep new blood from entering the isolated area or to leave, but insufficient to produce any physical discomfort or mental disturbance. The skin of the interdigital fold is shown as 12.

The light from source 14, is transmitted to the clamped area by optical pipe 16, and from the clamped area by pipe 18 to a light measuring and scanning device 20, employing a spectrometric means, which is capable of measuring the relative transmitted light values at various selected wavelengths. The transmitted light values are converted into electrical components and amplified sufficiently for measuring purposes by the converter 22, from which device the signals are fed into a display device such as an oscillograph or X-Y recorder 26.

A scan throughout the region from about 245 nanometers to about 600 of oxyhemoglobin is shown in FIG. 1. The apparatus will also show the scanned region between selected wavelengths and periodically rescan the selected area, desireably in one second or less time, depending on the accuracy desired.

Of all the sensitive areas of the oxyhemoglobin curve, showing a rate of change which is greater than the adjacent regions of the same curve during oxygen reduction, after occlusion, such as 245, 280, 350, 417, 548 and 578 nanometers, it appears that 578 is the most desireable for our purpose. Therefore the rapid scan technique shown in FIG. 2. illustrates the change in the spectral curve for oxyhemoglobin from the moment of occlusion, to the moment when the relative transmission has reached the same value for the 578 nanometer wavelength, regions as for the 565 nanometer wavelength region.

In place of the interdigital clamp, a tourniquet may be used, about the upper arm or even around a finger. Instead of transmitted light, reflected light from the skin will similarly pick up the oxyhemoglobin especially if erythema is produced by rubbing the skin or by the use of chemicals.

In place of a scanning spectrophotometer, inferference filters may be used having selected nanometer ratings. A recording spectrophotometer made by the American Optical Company employed a mirror mounted on a vibrating reed. The reflected light from the mirror, scanned the spectrum with each oscillation of the reed, and produced a visual image of the spectral curve on an oscilloscope with each reed vibration. Thus a scan of one-sixtieth of a second is possible.

The time required for the oxyhemoglobin to be reduced from the position shown in FIG. 2, at the lowest point at the 578 region curve starting from the moement of occlusion, namely 34, to reach the same level of the change as does the peak 32 of the same curve 30, is 25 seconds for the particular individual tested. This occurs when 32b reaches the same level as 32a. This time period for an individual is designated as the reduction time. It is also correlated to the rate of oxygen utilization by the tissue. It will be noted that the sensitive part of the curve, namely the portion designated as 34, shows a fast reduction beyond the point 32b, as is indicated in the 30 second scan where the point of inflexion of the curve is reversed.

In the space-time relationship uniquely set forth, it is possible to use a measured change in the relationship where instead of time being the variable, the time is constant and the space change is measure for a fixed period of time. This places a limitation on the instrument used, and is a more limited determination. As presently employed the time designation representing an inner change requirement of the oxyhemoglobin curve is independent of the instrument used, the thickness and character of the skin, and especially its pigmentation.

It has been confirmed that the rate of oxygen utilization is a measure of the individual's degree of homeostasis. A reduction time below 25 seconds appears to indicate some form of dysfunction. An increased efficiency in oxygen utilization is represented by a rate of utilization of 25 seconds or more, and readings have been taken to 70 seconds.

The test is an extremely sensitive one, since the body at rest and in motion will have different rates of oxygen utilization. Since the test is noninvasive, the adrenal shock caused by blood withdrawal does not enter into the reading and does not modify or destroy its accuracy.

Moreover, if an accelerated rate of oxygen utilization is found, for example of 18 seconds, and treatment is undertaken to correct the dysfunction, if the change in the rate of oxygen utilization is not in the direction of homeostasis, it can be assumed that the treatment is not adequate or even harmful. This applies to drug doses which may be effective only in specific amounts.

The foregoing method of measuring the rate of oxygen utilization is as simple as the use of a thermometer for reading body temperature. Like the thermometer, the reading merely discloses some interference in oxygen utilization. Unlike a thermometer, it is a far more sensitive measurement and will show a disfunction where a thermometer will show a normal reading. Moreover, it can be used to indicate the effectiveness of remedial procedures.

To insure safety of the sensitive instruments, and accuracy in reading, the clamp should be provided with electrical contacts and circuits to start the light source and the timing mechanism, only when the clamp is closed upon the tissue.

This may be accomplished by providing a pressure-sensitive switch 52 between the arms 10a of the clamp 10, to close the circuit between lead 46 connected to the light measuring and scanning apparatus 20, to the light source 14, only when the clamp is closed upon the tissue. This will allow the light to enter the light sensitive apparatus only when the tissue intervenes, and to disconnect the light before the clamp can be removed from the tissue. Thus the complete circuit from the power source 42 is through lead 44 to the apparatus 20 and lead 40, to the light source 14.

In FIG. 4, I have shown an apparatus which employs two interference filters, as described above, to provide two selected regions of light through the clamped tissue. The light is converted into electrical values and transmitted to a comparator, to determine the rate of oxygen utilization as measured by a digital timer which is started when the clamp is closed on the tissue, and the timer is stopped when the comparator determines that the two spectral values measured are equalized.

More specifically the light selecting unit 20c is a rotating disc 20d in which the two selected filters 20e, and 20f are positioned. A motor 20g rotates the disc; alongside two Hall-effect sensors 20h and 20j are positioned to electrically signal a light converting unit 22c, when each of the filters is in position for transmitting light. A small magnet 20k in position on the disc actuates the sensor positioned adjacent thereto, at the proper moment in the rotation of the disc.

The light passes through pipe 16c, through interference filter 20f, when rotated in proper position, into pipe 18c, through apertured clamp 10c and the interdigital fold 12c supported therein, into photocell 22d where it is electrically converted into an electrical impulse which is fed into one half of the bilateral switch 22e, which is actuated by the sensor corresponding to the filter, namely 20j. As the disc rotates the filter 20e is positioned in the light beam in the optical pipe, and the photocell 22d responds thereto, while the sensor 20h actuates the other half of the bilateral switch 22e. The sensors are connected to the bilateral switch through leads A and B respectively.

By proper loading of the current passing through leads A and B, the leading current from the filters may be delayed to make a comparison of the spectral values practically simultaneously.

When the spectral values are compared and are found to be equalized by the comparator 60, into which is fed the two signals through leads 60a and 60b, by the bilateral switch 22e, the comparator will through the stop-start connection 60c, stop the digital timer 26c at the precise moment that the two signals are found to be equalized by the comparator.

As has been previously stated the critical rate of oxygen utilization has been found to be 25 seconds, as observed subjectively. The rate of oxygen utilization, by the criteria previously established in clinical testing, measured in seconds may thus be electronically determined by the apparatus thus described.

After a determination has been made by the digital timer which has stopped at the determined rate, the stop-start unit 60c may be made to operate a power distribution multiple switch relay 62, which may require a flip-flop switch 64, through lead 66, to open the circuit which supplies power to the light selecting and converting units 20c and 22c, through lead 22Y, 22Y', and 20X; to the light source 14c through lead 40W, the latter when the clamp is opened through clamp switch 52e.

However the timer 26c is supplied power continuously through the relay, and is controlled by supplementary switch 52c in the clamp which is the only way to terminate power to the timer when the clamp is opened, thus disconnecting lead 26Z from the relay to the clamp before this is done, the reset switch 66 should be actuated through lead 62S and 66S, through the switch 52d in the clamp, to reset the digital timer back to zero for subsequent use in another determination.

The clamp switch 52d can be eliminated, as can all the other switches illustrated by manually opening and closing the circuits when necessary.

The apparatus is started by compressing the clamp on a fold in the skin which starts the light, the rotary disc, activates the sensors, the photocell, the bilateral switch, the comparator and the digital timer. The two filters are operable to transmit light in the regions of 565 and 578 nanometers, which happen to be in the visible spectrum. When the coefficients of absorption are equalized, as the oxygen is reduced unequally as scanned in the two regions, one coeficient over takes the other. At this precise moment the comparator will stop the timer which will then indicate the elapsed time from the moment of occlusion, for the person tested.

In place of the rotary disc, carrying the two filters, the full light from the source 14c may be directly routed through the clamp and skin into two side by side photodetectors, one having a peak sensitivity at 565 n.m. of light, and the other with a peak sensitivity at 578 n.m. each of which are connected to the bilateral switch as shown in FIG. 4, which should produce the identical results.

I have thus described various forms of apparatus for carrying out the invention, but I desire it understood that the invention is not confined to the particular forms shown and described, the same being merely illustrative, and that the invention may be carried out in other ways following the teachings here disclosed, without departing from the spirit of my invention.

I claim the following:

1. A non-invasive, spectrometric measuring apparatus for objective in vivo determination of the rate of oxygen utilization in peripheral tissue, comprising:
   tissue encircling clamping means for isolating a segment of blood in the tissue of the skin to thereby produce a state of occlusion whereby oxygen absorption may be analyzed,
   means for detecting coefficients of absorption for oxyhemoglobin in said tissue in at least first and second wavelength regions after occlusion and during a time interval, said first and second wavelength regions having different rates of change of absorption coefficient when said tissue is in an occluded state, said means for detecting providing electrical output values indicative of the absorption coefficient in said first and second wavelength regions during the time interval, and
   means coupled to the output of said detection means for determining the rate of change of said absorption coefficient in said first wavelength region relative to the rate of change of said absorption coefficient in said second wavelength region and for producing an output therefrom which is indicative of the rate of oxygen utilization in said tissue.

2. The apparatus of claim 1, in which the spectral regions are selected in which the coefficients of absorption of one region, become equal to the coefficients of absorption of the other region, and means are provided for measuring the elapsed time after the peripheral tissue is clamped, to the moment when the coefficients become equal.

3. The apparatus of claim 1, in which a recorder is provided for visually registering intermittent scans of the coefficients of absorption of both selected spectral regions of the oxyhemoglobin in the isolated blood; and said means for determining determines the elapsed time between scans, so that the rate of oxygen utilization can be determined by counting the number of scans from the moment of blood isolation to the registered scan in which the said coefficients of absorption in the registered scan are equal in value.

4. The apparatus of claim 1, provided with a timer; means for starting the timer at the moment of blood isolation; and electronic means for comparing the electrical values corresponding to the spectral values of the coefficients of absorption of both spectral regions; and means for indicating on the timer when the coefficients of absorption of both selected regions are equal in value.

5. The apparatus of claim 1, provided with a comparator for comparing the electrical values of the changing coefficients of the two spectral regions; and means for controlling an electric timer to record the time from the moment of blood isolation to the moment of equalization of the coefficients of absorption of the two spectral regions.

6. The apparatus of claim 1, in which a timer is provided for registering the time that has elapsed from the moment of blood isolation to the moment when the coefficients of absorption of the two spectral regions are equalized.

7. The apparatus of claim 1, in which a timer is provided; means for starting the timer at the moment of blood isolation; and means for stopping the timer when the coefficients of absorption of the two spectral regions are equalized.

8. The apparatus of claim 1, in which the spectrometric measuring apparatus includes a light source, and means are provided for discontinuing the light source when the clamping means is released.

9. The apparatus of claim 1, in which the spectrometric measuring apparatus includes a light source, and means are provided for starting the light source when the clamp is applied to the tissue.

10. The apparatus of claim 1, in which the spectrometric measuring apparatus includes includes two light measuring means for detecting light in the spectral regions of 565 and 578 nanometers.

* * * * *